(12) United States Patent
Lituev

(10) Patent No.: US 10,973,467 B2
(45) Date of Patent: Apr. 13, 2021

(54) METHOD AND SYSTEM FOR AUTOMATED DIAGNOSTICS OF NONE-INFECTIOUS ILLNESSES

(71) Applicant: Victor Lituev, Moscow (RU)

(72) Inventor: Victor Lituev, Moscow (RU)

( * ) Notice: Subject to any disclaimer, the term of this patent is extended or adjusted under 35 U.S.C. 154(b) by 259 days.

(21) Appl. No.: 16/350,700

(22) Filed: Dec. 26, 2018

(65) Prior Publication Data

US 2020/0000413 A1    Jan. 2, 2020

(51) Int. Cl.
*A61B 5/00*    (2006.01)
*G16H 50/20*    (2018.01)

(52) U.S. Cl.
CPC ......... *A61B 5/7264* (2013.01); *A61B 5/7282* (2013.01); *G16H 50/20* (2018.01)

(58) Field of Classification Search
CPC .... A61B 5/7264; A61B 5/7282; G16H 50/20; G16H 50/30
USPC ........................................................ 600/301
See application file for complete search history.

*Primary Examiner* — Amanda K Hulbert
*Assistant Examiner* — Philip C Edwards

(57) ABSTRACT

According to examples, an apparatus may include a processor and a memory on which is stored machine readable instructions executable by the processor to access test parameters of a patient; calculate average values for each of the accessed test parameters having a reference value range and assign binary coefficient values to the accessed test parameters based on comparison of the average value to the range limits; assign binary coefficient values to the accessed test parameters that do not have the reference value range based on a test parameter presence; generate a patient parameter matrix based on the assigned binary coefficient values; and apply statistical processing to the patient parameter matrix to make a diagnosis.

6 Claims, 3 Drawing Sheets

METHOD AND SYSTEM FOR AUTOMATED DIAGNOSTICS OF NONE-INFECTIOUS ILLNESSES

BACKGROUND

Making a medical diagnosis based on a large volume of medical test and patient-related data reflecting a state of the patient becomes a difficult task. Even if the data is classified and aggregated, the accurate diagnosis may not be achieved. In many instances important for accurate diagnostics data may be ignored, because some of the data is not comparable. A convention biochemical blood test produces many parameters measured in different measurement units, such as for example, hemoglobin is measured in g/dl, platelets are measured in E9/L, glucose is measured in mmol/L, and etc. At the initial stage of diagnosis, a doctor may decide how to classify all test data for a given patient based on the doctor's experience and intuition in order to determine key pathological parameters.

Given a large variety of test parameters and connections between the test parameters, the classification may not be sufficient and may not assist the doctor in making a correct diagnosis. The statistics-based methods may be useful for medical test data classification, but for a large group of patients. RF patent No. 2141247 issued in 1999 discloses a statistics-based method for diagnostics of infectious diseases. A variety of parameters are collected for a group of patients and mathematically processed to determine a set of key diagnostic parameters that may indicate a presence of illness in a patient based on deviation of the key parameters from a statistical norm. The main shortcoming of this method is a poor diagnostic accuracy of a none-infectious diseases in a single patient, because the diagnosis is made based on average data calculated on a large group of patients. According to the method disclosed in the above patent, in order to determine a cause or causes of illness, the factors affecting this illness are defined. However, these factors affect development of this illness not in the given patient, but over a large group of average patients. Accordingly, if the given patient is close to the average patient in terms of measured medical parameters, the diagnosis and possible causes of the illness may be determined fairly accurate. However, the further is a particular patient from the average patient, the less accurate the diagnosis and possible illness causes become. Accordingly, it is desired to have a system and method for automated diagnostics of a patient's none-infectious illness and for determination the causes of the illness for an individual patient based on the patient's test results.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1:
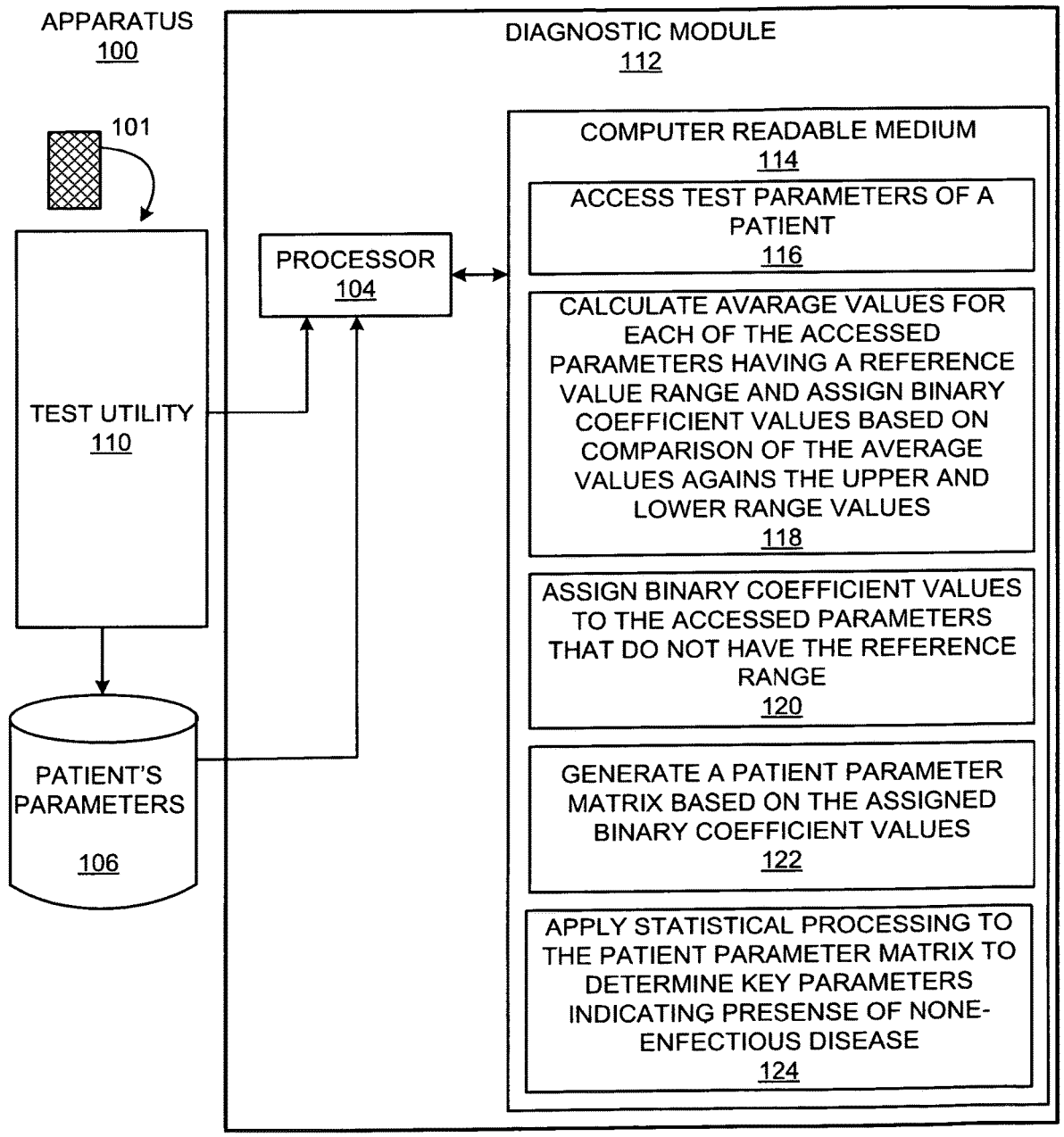
FIG. 1 illustrates an example apparatus that may provide for an automated diagnosis of none-infections disease in an individual patient.

For simplicity and illustrative purposes, the present disclosure is described by referring mainly to examples. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on.

Disclosed herein is a system and a method for automated diagnostics of none-infectious diseases based on measured individual patient's medical test parameters defining a current health condition of the patient. According to an exemplary embodiment, the test parameters may be processed by statistical methods in order to determine some key parameters having known normal values. Any deviation of these key parameters from the normal values may indicate a presence of a none-infectious disease. This approach allows to overcome some of the shortcomings of the know methods discussed above. In particular, the method and system in accordance to the exemplary embodiment may provide for more accurate diagnosis of none-infectious disease in individual patients by utilizing additional key factors indicating development of the disease in a given patient. The process of making the diagnosis is advantageously automated. That is, testing specimen, such as for example, blood, urine, culture, etc. may be placed into a testing apparatus having an integrated diagnostic module that automatically processes the test results and outputs the diagnosis to a doctor. In one embodiment, a diagnostic module may receive additional data inputted by the doctor or a lab technician such as for example patient's age, gender, medical history-related data etc.

According to the exemplary method, for the test parameters that have reference ranges, the method may calculate an average value between the upper range value, the patient's test value and the lower range value. For the rest of the test parameters binary values ("0" or "1") are used as follows:

if a certain parameter is present, a value of "1" is used, otherwise it is considered to be "0";

if a certain parameter is within the reference range (i.e., is normal), a value of "1" is used, otherwise it is considered to be "0";

if a certain parameter is higher than the upper reference range value (i.e., is above the normal value), a value of "1" is used, otherwise it is considered to be "0"; and if a certain parameter is below the lower reference range value (i.e., is below the normal value), a value of "1" is used, otherwise it is considered to be "0".

if a volatility of a parameter value is within a range of 0%-3.0% of reference values and the variation coefficient for the parameter (calculated based on dispersion data) is within the volatility range, a binary value may be assigned to the parameter;

if a volatility of a parameter value is within a range of 3.01%-10.0% of reference values and the variation coefficient for the parameter (calculated based on dispersion data) is within the volatility range, a binary value of "1" may be assigned to the parameter, otherwise "0" is assigned;

if a volatility of a parameter value is within a range of 10.01%-20.0% of reference values and the variation coefficient for the parameter (calculated based on dispersion data) is within the volatility range, a binary value of "1" may be assigned to the parameter, otherwise "0" is assigned;

if a volatility of a parameter value is within a range of 20.01%-30.0% of reference values and the variation coefficient for the parameter (calculated based on dispersion data) is within the volatility range, a binary value of "1" may be assigned to the parameter, otherwise "0" is assigned;

if a volatility of a parameter value is within a range>30.1% of reference values and the variation coefficient for the parameter (calculated based on dispersion data) is within the volatility range, a binary value of "1" may be assigned to the parameter, otherwise "0" is assigned; and if a value of the test parameter below the average value calculated for the particular patient based on the test value and the upper and the lower range values, the parameter is assigned value of "1", otherwise "0".

According to the exemplary embodiment, a patient parameter matrix may be generated based on the above binary values. A number of intervals across the rows of the matrix may change in the direction of increasing their divisibility. The following formula for calculation for the average values may be used:

$$\bar{x} = \frac{x_1 + x_2 + x_3 + x_4 + \ldots + x_n}{n}$$

A standard deviation (i.e. dispersion) may be calculated as follows:

$$\sigma^2 = \frac{\sum (x - \bar{x})^2}{n}.$$

Variation coefficient may be calculated as:

$$V = \frac{\sigma}{\bar{x}} \times 100\%$$

As discussed herein, based on the collection of the above binary values, the diagnostic module may generate an individual patient matrix reflecting patient's clinical and biochemical state. The individual patient matrix includes all of the above binary coefficients calculated based on available reference values for each of the tested parameters. According to the exemplary embodiment, the individual patient matrix may be processed to determine the key parameters affecting current patient's condition and indicating a possibility of presence of a none-infectious disease in this patient. Additionally, the diagnostic module may determine dependency links between the key parameters that may be critical for determining a presence and a structure of a particular pathology caused by the disease in the patient. Note that the method disclosed herein may use a broader selection of initial patient-related data that includes not only medical parameters defined by number in units, but parameters that are simply defined by their presence or lack thereof. The diagnostic module may determine the effect caused by some test parameters over other patient's parameters and may determine groups of linked parameters. Note that the presence of the links between generally independent medical parameters may be used as a basis for analysis and efficient diagnosis of a particular disease in the patient.

For example, in case of oncological pathology, the doctor may be able to determine a combination of parameters or a single parameter that determine a course of development of oncological adenoma and possibilities of successful remission. Accordingly, this automated diagnosis may allow the doctor to come up with the most effective treatment plan. Note that the proposed approach relies on statistics related to the individual patient rather than conventionally used statistics applied to a group of patients. Thus, a precise treatment plan for the given patient is produced instead of a generic average-based treatment plan.

In one embodiment, the diagnostic module may determine the key parameters by defining a group of parameters that have particular interdependencies between the parameters within the group. This approach allows for determining the dependencies between the parameters that indicate pathology, because these parameters are always independent in a healthy patient. In yet another embodiment, the diagnostic module may process the patient's individual matrix using cluster analysis to determine structural dependencies from all possible dependencies between patient's medical parameters. Thus, groups of the interdependent parameters may be determined. These parameters affect each other within the group, but may have no impact over parameters within other groups.

In yet another embodiment, the diagnostic module may process the patient's individual matrix using factor analysis to determine changes factor weights and directions of propagation (i.e., pluses and minuses) for each of the parameters when the parameters are being affected by each of the parameters from a plurality of the patient's parameters available. Alternatively, or in addition to the approaches disclosed herein, the diagnostic module may process the patient's individual matrix by multiple regression method in order to determine an influence of independent parameters over dependent patient's parameters. In yet another embodiment, the diagnostic module may process the parameters that have reference values to correct the reference values based on a set of patient's test parameters' values collected over a period of time. This approach produces a set of reference values for the given patient for a particular time period. This approach, advantageously, improves the accuracy of analysis that use an extended set of the patient's parameters indicating the medical state of the patient over a period of time rather that at the give moment. Accordingly, random factors that may cause deviations of certain parameters from the norm are eliminated.

FIG. 1 illustrates an example apparatus that may provide for an automated diagnosis of none-infections disease in an individual patient in accordance with the exemplary embodiment. The apparatus 100 may include a test utility 110 including an integrated diagnostic module 112. In one embodiment, the test utility 110 may be coupled to the diagnostic module 112. The test utility 110 is configured to receive a patient test specimen 101 (e.g., blood, urine, saliva, etc.) and to perform the patient specimen analysis. The test utility 110 produces the patient's test parameters that may be accessed by a processor 104 of the diagnostic module 112. The patient's test parameters may be stored in a patient's parameters database 106 to be accessed by the processor 104. In one embodiment, the test parameters may be provided to the processor 104 of the diagnostic module 112 in real time. Additionally, some additional patient-related parameters such as, for example, gender, age, symptoms, medical history data, previously acquired test parameters and etc. may be entered into the test utility via a doctor's interface integrated into the test utility (not shown). In one embodiment, the wireless data input is provided by the integrated interface. The processor 104 may access the additional patient-related parameters from the patient's parameters database 106.

As discussed above, FIG. 1 shows an example apparatus 100 that may include the diagnostic module 112 for detecting a presence of the none-infectious disease in the patient. It should be understood that the apparatus 100 may include additional components and that some of the components described herein may be removed and/or modified without departing from a scope of the apparatus 100 disclosed herein.

The diagnostic module 112 may be a computing device, a tablet computer, a server computer, a Smart Phone, or the like, and may include a processor 104, which may be a semiconductor-based microprocessor, a central processing unit (CPU), an application specific integrated circuit (ASIC), a field-programmable gate array (FPGA), and/or another hardware device. Although a single processor 104 is depicted, it should be understood that the diagnostic module 112 may include multiple processors, multiple cores, or the like, without departing from a scope of the apparatus 100.

The diagnostic module 112 may also include a non-transitory computer readable medium 114 that may have stored thereon machine-readable instructions executable by the processor 104. Examples of the machine-readable instructions are shown as 116-124 and are further discussed below. Examples of the non-transitory computer readable medium 112 may include an electronic, magnetic, optical, or other physical storage device that contains or stores executable instructions. For example, the non-transitory computer readable medium 112 may be a Random Access memory (RAM), an Electrically Erasable Programmable Read-Only Memory (EEPROM), a hard disk, an optical disc, or other type of storage device.

The processor 104 may fetch, decode, and execute the machine-readable instructions 116 to access test parameters of a patient who's specimen 101 is analyzed by the test utility 110. As discussed above, the processor may execute the machine-readable instructions 116 to access test parameters from the test utility 110 in real time or from the patient's parameters database 106. The processor 104 may fetch, decode, and execute the machine-readable instructions 118 to calculate average values for each of the accessed parameters that have a reference value range. That Is, the processor 104 may calculate an average value between the accessed parameter value and the upper and the lower range values. Then, the processor 104 may fetch, decode, and execute the machine-readable instructions to assign a binary coefficient value (i.e., "1" or "0") to the accessed parameter based on comparison of the average value and the upper and lower range values of this parameter. In one example, if the average value falls below (or equals) the lower range value, the accessed (i.e., test) parameter may be assigned "0" value. If the average value exceeds (or equals) the upper range value, the accessed (i.e., test) parameter may be assigned "1" value. Other variations of the average value against the range values are discussed above in more detail (see paragraph 0010).

The processor 104 may fetch, decode, and execute the machine-readable instructions 120 to assign binary coefficient values to the accessed parameters that do not have the reference range. That is, the value of "1" is assigned if the parameter is present and the value of "0" is assigned if the parameter is absent. The processor 104 may fetch, decode, and execute the machine-readable instructions 122 to generate a patient parameter matrix based on the assigned binary coefficient values. The patient parameter matrix may have the binary coefficient values indicating presence or absence of the parameter by vertical columns and the binary coefficient values indicating parameter deviation within or outside of the reference range by horizontal rows. The processor 104 may fetch, decode, and execute the machine-readable instructions 124 to apply statistical processing to the patient parameter matrix to determine key parameters indicating presence of none-infectious disease in the patient.

Figure 2:
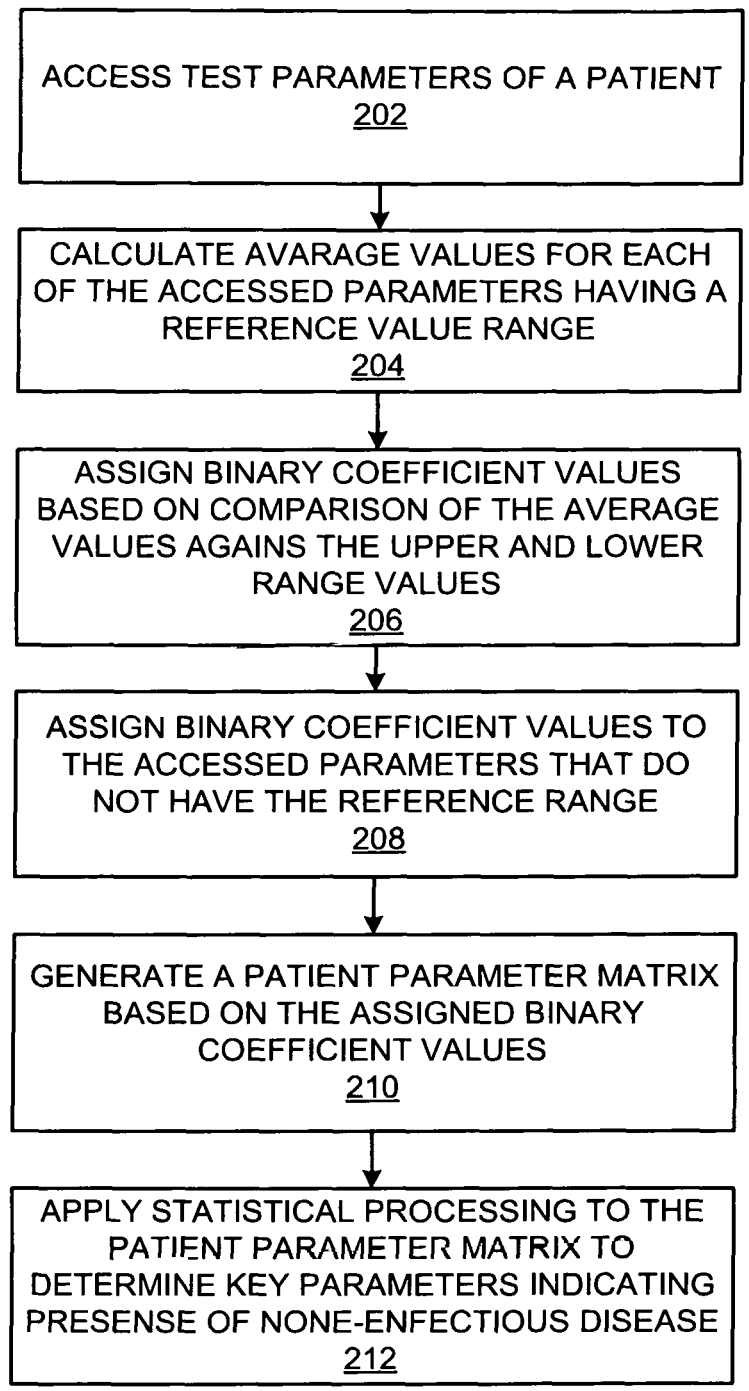
FIG. 2 illustrates a flow diagram of a method for automated diagnosis based on individual patient parameter matrix, in accordance with the exemplary embodiment.

Turning now to FIG. 2, there is shown a flow diagram of a method for automated diagnosis based on an individual patient parameter matrix, in accordance with the exemplary embodiment. It should be understood that method 200 depicted in FIG. 2 may include additional operations and that some of the operations described therein may be removed and/or modified without departing from the scope of the method 200. The description of the method 200 is also made with reference to the features depicted in FIG. 1 for purposes of illustration. Particularly, the processor 104 of the diagnostic module 112 may execute some or all of the operations included in the method 200.

With reference to FIG. 2, at block 202, the processor 104 may access test parameters of a patient who's specimen 101 is analyzed by the test utility 110, as shown in FIG. 1. At block 204, the processor 104 may calculate average values for each of the accessed parameters that have a reference value range. As discussed above with reference to FIG. 1, the processor 104 may calculate an average value between the accessed parameter value and the upper and the lower range values for this test parameter. Then, at block 206, the processor 104 may assign a binary coefficient value (i.e., "1" or "0") to the accessed parameter based on comparison of the average value and the upper and lower range values of this parameter. Subsequently, at block 208, the processor 104 may assign binary coefficient values to the accessed parameters that do not have the reference range. For example, the value of "1" is assigned if the parameter is present and the value of "0" is assigned if the parameter is absent. At block 210, the processor 104 may generate a patient parameter matrix based on the assigned binary coefficient values. At block 212, the processor 104 may apply statistical processing to the patient matrix to determine key parameters indicating a presence of none-infectious disease in the patient.

Through implementation of the method 200, the apparatus 100 may be able to produce a set of key parameters critical to correct diagnosis. Some or all of the operations set forth in the method 200 may be contained as utilities, programs, or subprograms, in any desired computer accessible medium. In addition, the method 200 may be embodied by computer programs, which may exist in a variety of forms. For example, the method 200 may exist as machine readable instructions, including source code, object code, executable code or other formats. Any of the above may be embodied on a non-transitory computer readable storage medium.

Examples of non-transitory computer readable storage media include computer system RAM, ROM, EPROM, EEPROM, and magnetic or optical disks or tapes. It is therefore to be understood that any electronic device capable of executing the above-described functions may perform those functions enumerated above.

Figure 3:
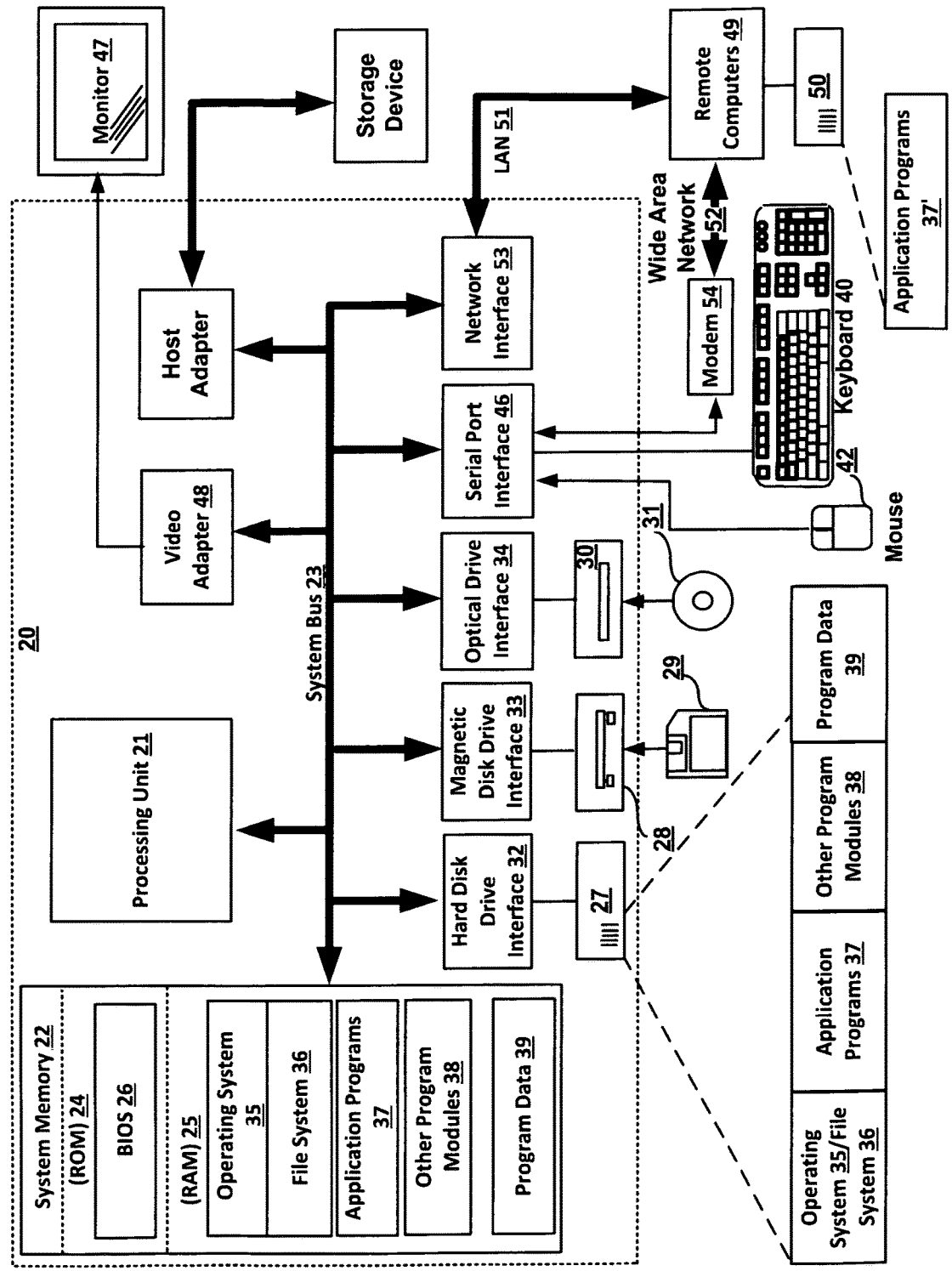
FIG. 3 illustrates a schematic diagram of a computer system or a server on which a diagnostic module may be implemented, in accordance with the exemplary embodiment.

With reference to FIG. 3, an exemplary system for implementing the diagnostic module 112 includes a general purpose computing device in the form of a host computer or a server 20 or the like, including a processing unit 21, a system memory 22, and a system bus 23 that connects various system components including the system memory to the processing unit 21.

The system bus 23 may be any of several types of bus structures including a memory bus or memory controller, a peripheral bus, and a local bus using any of a variety of bus architectures. The system memory includes a read-only memory (ROM) 24 and random access memory (RAM) 25. A basic input/output system 26 (BIOS), containing the basic routines that help to transfer information between the elements within the personal computer 20, such as during start-up, is stored in ROM 24.

The server 20 may further include a hard disk drive 27 for reading from and writing to a hard disk, not shown herein, a magnetic disk drive 28 for reading from or writing to a removable magnetic disk 29, and an optical disk drive 30 for reading from or writing to a removable optical disk 31 such as a CD-ROM, DVD-ROM or other optical media. The hard disk drive 27, magnetic disk drive 28, and optical disk drive 30 are connected to the system bus 23 by a hard disk drive interface 32, a magnetic disk drive interface 33, and an optical drive interface 34, respectively.

The drives and their associated computer-readable media provide non-volatile storage of computer readable instructions, data structures, program modules and other data for the server 20. Although the exemplary environment described herein employs a hard disk, a removable magnetic disk 29 and a removable optical disk 31, it should be appreciated by those skilled in the art that other types of computer readable media that can store data that is accessible by a computer, such as magnetic cassettes, flash memory cards, digital video disks, Bernoulli cartridges, random access memories (RAMs), read-only memories (ROMs) and the like may also be used in the exemplary operating environment.

A number of program modules may be stored on the hard disk, magnetic disk 29, optical disk 31, ROM 24 or RAM 25, including an operating system 35 (e.g., MICROSOFT Windows™ 2000). The server 20 includes a file system 36 associated with or included within the operating system 35, such as the Windows NT™ File System (NTFS), one or more application programs 37, other program modules 38 and program data 39. A user may enter commands and information into the server 20 through input devices such as a keyboard 40 and pointing device 42.

Other input devices (not shown) may include a microphone, joystick, game pad, satellite dish, scanner or the like. These and other input devices are often connected to the processing unit 21 through a serial port interface 46 that is coupled to the system bus, and they may also be connected by other interfaces, such as a parallel port, game port or universal serial bus (USB). A monitor 47 or other type of display device is also connected to the system bus 23 via an interface, such as a video adapter 48. In addition to the monitor 47, computers typically include other peripheral output devices (not shown), such as speakers and printers.

The server 20 may operate in a networked environment using logical connections to one or more remote computers 49. The remote computer (or computers) 49 may be another personal computer, a server, a router, a network PC, a peer device or other common network node, and it typically includes some or all of the elements described above relative to the server 20, although here only a memory storage device 50 is illustrated. The logical connections include a local area network (LAN) 51 and a wide area network (WAN) 52. Such networking environments are common in offices, enterprise-wide computer networks, Intranets and the Internet.

In a LAN environment, the server 20 is connected to the local network 51 through a network interface or adapter 53. When used in a WAN networking environment, the server 20 typically includes a modem 54 or other means for establishing communications over the wide area network 52, such as the Internet.

The modem 54, which may be internal or external, is connected to the system bus 23 via the serial port interface 46. In a networked environment, the program modules depicted relative to the server 20, or portions thereof, may be stored in the remote memory storage device. It will be appreciated that the network connections shown are merely exemplary and other means of establishing a communications link between the computers may be used.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example of the disclosure along with some of its variations. The terms, descriptions and figures used herein are set forth by way of illustration only and are not meant as limitations. Many variations are possible within the spirit and scope of the disclosure, which is intended to be defined by the following claims—and their equivalents—in which all terms are meant in their broadest reasonable sense unless otherwise indicated.

What is claimed is:

1. An apparatus comprising:
a diagnostic module;
a test utility operatively connected to the diagnostic module and configured to receive a patient test specimen;
a patient's parameters database configured to store patient's test parameters acquired from the patient test specimen by the test utility,
wherein the diagnostic module is configured to:
access the patient's test parameters from the patient's parameters database;
calculate average values for each of the accessed test parameters having a reference value range and assign binary coefficient values to the accessed test parameters based on comparison of the average value calculated between a test parameter value and an upper and lower range values against the upper range value and the lower range value of the value range;
assign binary coefficient values to the accessed test parameters that do not have the reference value range based on a test parameter presence;
generate a patient parameter matrix based on the assigned binary coefficient values; and
apply statistical processing to the patient parameter matrix to determine key diagnostic parameters indicating a presence of a none-infectious disease in the patient.

2. The apparatus of claim 1, wherein the instructions are further to cause the processor to determine the key diagnostic parameters by selecting a group from the accessed parameters, wherein the selected accessed test parameters have interdependencies within the group.

3. The apparatus of claim 1, wherein the instructions are further to cause the processor to apply statistical processing to the patient parameter matrix using cluster analysis to determine structural dependencies from all dependencies between the accessed test parameters.

4. The apparatus of claim 1, wherein the instructions are further to cause the processor to apply statistical processing to the patient parameter matrix using factor analysis to determine variations in factor weights and directions of each of the accessed test parameters under an impact from all of the accessed parameters.

5. The apparatus of claim 1, wherein the instructions are further to cause the processor to apply statistical processing to the patient parameter matrix using multiple regression to determine influence of independent accessed parameters over dependent accessed test parameters.

6. A method for an automated diagnosis comprising:
accessing, by a diagnosis module, test parameters of a patient;
calculating, by the diagnosis module, average values for each of the accessed test parameters having a reference value range;
assigning, by the diagnosis module, binary coefficient values to the accessed test parameters based on comparison of the average value calculated between a test parameter value and an upper and lower range values against the upper range value and the lower range value of the value range;
assigning, by the diagnosis module, binary coefficient values to the accessed test parameters that do not have the reference value range based on a test parameter presence;
generating, by the diagnosis module, a patient parameter matrix based on the assigned binary coefficient values; and
applying, by the diagnosis module, statistical processing to the patient parameter matrix to determine key diagnostic parameters indicating a presence of a none-infectious disease in the patient.

* * * * *